US012708792B2

(12) United States Patent
Pätilä et al.

(10) Patent No.: US 12,708,792 B2
(45) Date of Patent: Aug. 18, 2026

(54) KIT FOR TREATMENT OF PATIENTS HAVING DRY MOUTH SYNDROME

(71) Applicant: Koite Health Oy, Espoo (FI)

(72) Inventors: Tommi Pätilä, Espoo (FI); Sakari Nikinmaa, Espoo (FI); Juha Rantala, Espoo (FI)

(73) Assignee: Koite Health Oy, Espoo (FI)

( * ) Notice: Subject to any disclaimer, the term of this patent is extended or adjusted under 35 U.S.C. 154(b) by 329 days.

(21) Appl. No.: 18/039,979

(22) PCT Filed: Dec. 2, 2021

(86) PCT No.: PCT/FI2021/050842
§ 371 (c)(1),
(2) Date: Jun. 2, 2023

(87) PCT Pub. No.: WO2022/117925
PCT Pub. Date: Jun. 9, 2022

(65) Prior Publication Data

US 2024/0017087 A1 Jan. 18, 2024

(30) Foreign Application Priority Data

Dec. 2, 2020 (FI) ..................................... 20206241

(51) Int. Cl.
*A61N 5/06* (2006.01)

(52) U.S. Cl.
CPC ........... *A61N 5/062* (2013.01); *A61N 5/0603* (2013.01); *A61N 5/0625* (2013.01); *A61N 2005/0606* (2013.01); *A61N 2005/0659* (2013.01); *A61N 2005/0661* (2013.01); *A61N 2005/0663* (2013.01)

(58) Field of Classification Search
CPC ................. A61N 5/06–2005/073; A61C 19/06
See application file for complete search history.

(56) References Cited

U.S. PATENT DOCUMENTS

| | | | | |
|---|---|---|---|---|
| 10,646,319 | B2 * | 5/2020 | Johansson | A61Q 11/00 |
| 2004/0193235 | A1 * | 9/2004 | Altshuler | A61N 5/0603 607/88 |
| 2011/0207075 | A1 * | 8/2011 | Altshuler | A61L 27/46 433/29 |
| 2015/0164618 | A1 * | 6/2015 | Heacock | A61C 1/0046 433/2 |
| 2017/0189153 | A1 * | 7/2017 | Johansson | A61C 19/06 |

FOREIGN PATENT DOCUMENTS

| | | | |
|---|---|---|---|
| CN | 109432608 | A | 3/2019 |
| KR | 20200027407 | A | 3/2020 |
| WO | WO2019222492 | A1 | 11/2019 |
| WO | WO2020084199 | A1 | 4/2020 |
| WO | WO2020193870 | A1 | 10/2020 |
| WO | WO2021178655 | A1 | 9/2021 |

OTHER PUBLICATIONS

Nemeth et al: The impact of photobiomodulation of major salivary glands on caries risk. Lasers in Medical Science, Jul. 17, 2019, vol. 35, No. 1, pp. 193-203.

* cited by examiner

*Primary Examiner* — Jonathan T Kuo
(74) *Attorney, Agent, or Firm* — Laine IP Oy

(57) ABSTRACT

Kit and method for treatment of patients having dry mouth syndrome. The kit comprises an odontological mouthpiece which has one or more light sources for producing light in the near-infrared range and which, once placed in the oral cavity, is capable of directing the light against target tissue selected from salivary glands, submandibular glands or both, for use in treatment of patients having dry mouth syndrome. The kit and the method can be used for treating Sjögren's syndrome, polypharmacy patients, diabetic patients or patients having a reduced number of salivary glands in particular causing a marked decrease, temporary or permanent in saliva production.

21 Claims, No Drawings

KIT FOR TREATMENT OF PATIENTS HAVING DRY MOUTH SYNDROME

FIELD OF THE INVENTION

The present invention relates to the treatment of patients suffering from the dry mouth syndrome. In particular, the present invention provides a kit comprising an odontological mouthpiece which has one or more light sources for use in a method of treating a patient having dry mouth syndrome. Further, the present invention provides a method of increasing the saliva secretion of patients having dry mouth syndrome.

BACKGROUND

Dry mouth is a condition in which there is a decreased production of saliva by the salivary glands. This condition is also referred to as xerostomia. Dry mouth can be a side effect of medications or radiation therapy for cancer, or it can be caused by conditions that directly affects the salivary glands, such as surgery, e.g. pharyngectomy, or Sjögren's syndrome which is an autoimmune disease.

Dry mouth is not merely a discomfort but can also be painful and involve health hazards, potentially leading to tooth decay, loss of ability to taste, difficulties in chewing and swallowing as well as to indigestion conditions.

Treatment for dry mouth typically depends on the cause. In the art, it has been proposed to use artificial salivas as well as various compositions that increase the flow of resting or unstimulated saliva.

There is a need for alternative methods of treating dry mouth conditions.

SUMMARY OF THE INVENTION

It is a first aim of the invention to provide a kit for use in treatment of patients having dry mouth syndrome.

It is a second aim of the invention to provide a method of increasing saliva secretion for patients having dry mouth syndrome.

According to an aspect of the present invention a kit is provided which comprises an odontological mouthpiece which has one or more light sources for producing light at least in the near-infrared range. When the mouthpiece is placed in the oral cavity, light from the light sources is directed against target tissue for increasing the production of saliva in the mouth. Thus, typically, the mouthpiece is adapted to producing light, such as non-coherent light, that is directed against the salivary glands or submandibular glands or both.

According to another aspect of the present invention, in a method of treating a patient having dry mouth syndrome, the patient's salivary glands, submandibular glands or both are subjected to non-coherent light in the near-infrared range by using an odontological mouthpiece which has one or more light sources capable for producing such light.

More specifically, the present invention is characterized by what is stated in the characterizing parts of the independent claims.

Considerable advantages are obtained by the invention.

The present invention will increase greatly saliva secretion and achieve rapid relieve for patients suffering from dry mouth syndrome. When the salivary glands or submandibular glands are subjected to light or heat, or a combination thereof, according to the present invention, tissue hormones will be secreted which regulate and stimulate excretion of saliva. The effect will rapidly set on and have a prolonged duration.

The present invention can be used for successfully treating Sjögren syndrome, polypharmacy patients, diabetic patients or patients having a reduced number of salivary glands in particular causing a marked decrease, temporary or permanent in saliva production.

In preferred embodiments, a mouthpiece with light sources is used intraorally. Such a mouthpiece typically takes up the shape of the dental arch and is user friendly and allows for treatment for extended time intervals, which increases the efficiency of the treatment.

By a treatment of the present kind, a hormonal and neurogenic response will be achieved. The glands will be stimulated by photobiomodulation or by heat directly directed to the gland, or by both. This action will achieve humoral stimulus of the glands.

Increased metabolism through increased blood flow will also stimulate the nerves, such as the trigerminal nerve. At the same time, stimulation of dental pulp will lead enhance saliva secretion. Heperemia will be increased.

In one embodiment, the light sources employed are adapted to subjecting the target tissue to light in the 380 to 450 nm, in particular about 405 nm, range and/or in the 780 to 830 nm, in particular about 810 nm, range, to achieve dilatation of blood vessels via nitric oxide release in the blood vessels, thus improving microcirculation.

Further, a combination of UV (for example about 405 nm) and IR (for example about 810 nm) light will have a combined synergic effect.

In one embodiment, the light sources are capable of increasing the production of antioxidant enzymes in the target tissue.

In one embodiment, increased saliva secretion for patients suffering from dry mouth syndrome is achieved in combination with antibacterial treatment of intraoral surfaces.

In the following, further features of the present invention will be discussed in relation to various embodiments.

EMBODIMENTS

The present technology provides for a mouthpiece for use in the treatment of dry mouth conditions.

In one embodiment, the mouthpiece produces light and can optionally be used together with a photosensitizer, such as indocyanine. Thus, in one embodiment, the effect of the mouthpiece is based on the provision of light stimulation.

In one embodiment, the effect of the mouthpiece is based on the provision of heat stimulation.

In one embodiment, the effect of the mouthpiece is based on a combination of heat and light stimulation.

In one embodiment, the kit comprises light sources which are capable of or adapted to producing non-coherent light with photons having majority energy in the range from 1.24 eV to 2.48 eV.

In one embodiment, the kit comprises light source which are capable of or adapted to producing light of the following energy levels: a first light with photons having a majority energy in the range from 3.5 eV to 2.8 eV, and a second light with photons having a majority energy in the range from 1.24 eV to 2.48 eV. Preferably, photons of the first light and the second light are simultaneously directed against the target tissue.

In one embodiment, the light sources are capable of or adapted to producing first light having a wavelength in the range of about 350 to 450 nm, for example about 370 to 410 nm, such as about 405 nm, and they are capable of or adapted to producing second light having a wavelength in the range of about 500 to 1000 nm, for example about 780 to 830 nm, such as 810 nm, or a combination thereof.

In one embodiment, light at a wavelength in the range of 350 to 450 nm, for example 405 nm, is employed for light stimulation. Light at a wavelength of 405 nm dilates blood vessels via nitric oxide release in blood vessels, and thus improves microcirculation. Light at a wavelength of 350 to 450 nm, in particular 405 nm, is also absorbed by erythrocytes (red blood cells), which has a positive rheological effect, including reduction in erythrocytes aggregation and deformability.

Further, light in the range of 780 to 830 nm, e.g. 810 nm, penetrates tissues and increases the intracellular NO production deeper in tissues, while the 350 to 450 nm, e.g. 405 nm, light does not penetrate deeply in tissues and increases the intracellular NO production in the relatively more in the surface area of the exposed area. Thus, the action of dual-light exposure is different than separately applied 780 to 830 nm, in particular 810 nm, or 350 to 450 nm, in particular 405 nm, light.

Using such light, the blood antioxidant capacity and lipid profile are also improved. These actions both increase the effect of NIR light, for example light at a wavelength of 780 to 830 nm, but also have their own separate mechanism in the dual-light action regarding the improvement of salivary gland function.

For example, in Sjögren's syndrome, the reduced production of antioxidant enzymes can be mechanistically targeted by the 350 to 450 nm, in particular 405 nm, light.

Similarly, these actions are further strengthened by NIR light which has similar actions, but activated by different pathways, due to activation of different chromophores in tissues and the flowing blood itself.

In one embodiment, the light sources comprise optoelectronic devices, such as one or more light emitting diodes (LEDs).

In one particular embodiment, the light sources are capable of or are adapted to producing a first light having a wavelength of 405 nm±10 nm and second light having a wavelength of 810 nm±15 nm. Preferably, the first and the second lights comprise non-coherent light, for example light produced by optoelectronic devices, such as one or more light emitting diodes (LEDs).

In one embodiment an intraoral mouthpiece is used which comprises

- a body made of a heat conducting material, the body further having an upper surface and an opposite lower surface, the surfaces comprising an essentially planar portion between lingual edges and buccal or labial edges, respectively, and configured to be placed against teeth surfaces, and
- a plurality of light sources attached to the body and adapted to deliver light to target tissue selected from salivary glands or submandibular glands or both.

Preferably, the light sources are embedded in a material, such as a polymeric material, which can be transparent. In one embodiment, the polymeric material comprises a silicon material. The polymeric material may have a taste which stimulates the secretion of saliva.

In one embodiment, the polymeric material in which the light sources are embedded is capable of buffering heat.

In one embodiment, the light sources consist of LEDs. One or more of the LEDs can be configured to emit light of only one wave length.

In one embodiment, one of more of the LEDs is/are configured to emit light of two or more wave lengths, such as light in the range of 350 to 450 nm, for example 380 to 430 nm, or 400 to 420 nm, and light in the range of 780 to 830 nm.

In one embodiment, the body of the mouthpiece comprises a heat dissipating (or hear conducting) tray. The tray typically has an extended portion, in particular at the front end (in use position), which forms a cooling tray or surface.

In one embodiment, the mouthpiece comprises planar and tilted surfaces and at least a part of the light sources is positioned on at least one of the tilted buccal, labial or lingual edges of the body.

In one embodiment, the position of the light sources or the surfaces can be configured such that the light is directed towards either the salivary glands and/or submandibular glands or dental pulp or both.

In one embodiment, at least 30%, preferably at least 50%, of the light sources are configured such that the light is directed towards the salivary glands and/or submandibular glands and at least 30% of the light sources are configured such that the light is directed towards the dental pulp.

In one embodiment, the light sources are capable of subjecting the target tissue to light which is being absorbed by erythrocytes.

In one embodiment, the patients are selected from the group of patients suffering from the Sjögren syndrome, polypharmacy patients, diabetic patients or patients having a reduced number of salivary glands in particular causing a marked decrease, temporary or permanent in saliva production.

In one embodiment, the patient suffers from the Sjögren syndrome or from type 1 or type 2 diabetes.

In one embodiment, a patient suffering from dry mouth is subjected to light, at least 30% of which (calculated from the total energy of the light) comprises light in the 780 to 830 nm range, and preferably at least a portion of which—typically about 10 to 80% (calculated from the total energy of the light)—is directed towards the dental pulp.

In one embodiment, a patient suffering from dry mouth is subjected to light, at least 30%, in particular at least 50% of which (calculated from the total energy of the light) comprises light in the 780 to 830 nm range, and at least 10% of which (calculated from the total energy of the light) comprises light in the 350 to 450 nm range, for example 380 to 430 nm, and preferably at least a portion of the light in the 780 to 830 nm range—typically about 10 to 80% of said light (calculated from the total energy of the light)—is directed towards the dental pulp.

In one embodiment, the mouthpiece of the kit is adapted to producing light at least 30%, in particular at least 50%, of which (calculated from the total energy of the light) consists of light in the 780 to 830 nm range, which mouthpiece is preferably further adapted to directing at least 10%, in particular 10 to 80%, of the light in the 780 to 830 nm range towards the dental pulp once it is placed in the oral cavity.

Stimulation of the dental pulp using light in the 780 to 830 nm range will effectively promote saliva excretion.

In one embodiment, a patient suffering from dry mouth is subjected to light, at least 30%, in particular at least 50% or at least 70% of which (calculated from the total energy of the light) comprises light in the 780 to 830 nm range, and preferably at least a portion of which—typically about 10 to 80% (calculated from the total energy of the light)—is directed towards the salivary glands, submandibular glands or both.

In one embodiment, the mouthpiece of the kit is adapted to producing light at least 30%, in particular at least 50%, of which (calculated from the total energy of the light) consists of light in the 780 to 830 nm range, which mouthpiece is preferably further adapted to directing at least 10%, in particular 10 to 80%, of the light in the 780 to 830 nm range towards salivary glands, submandibular glands or both once it is placed in the oral cavity.

Stimulation primarily of the salivary glands, submandibular glands or both dental pulp using light preferably in the 780 to 830 nm range will promote saliva excretion among patients suffering from loss of dental pulp.

In one embodiment, a patient suffering from dry mouth is subjected to light, at least 30%, in particular at least 50% or at least 70% of which (calculated from the total energy of the light) comprises light in the 780 to 830 nm range, and at least 10% of which (calculated from the total energy of the light) comprises light in the 350 to 450 nm range, for example 380 to 430 nm, and preferably at least a portion of the light in the 780 to 830 nm range—typically about 10 to 80% of light in the 780 to 830 nm range (calculated from the total energy of the light)—is directed towards the salivary glands, submandibular glands or both and at least 10 to 80% of light in the 350 to 450 nm range (calculated from the total energy of the light) is directed towards the dental pulp.

In one embodiment, the kit further comprises an agent selected from the group of salivary stimulants, such as Salagen (pilocarpine) and Evoxac (cevimeline hydrochloride).

In one embodiment, the kit further comprises at least one photosensitive substance for treating the target tissue using photodynamic therapy.

In one embodiment, the photosensitive substance is selected from the group of Hypericin, curcumin, phenalenone derivatives, Cercosporin, psoralen, xanthotoxin, Angelicin, alpha-Terthienyl, Phenylthepatriyne, THC, Cannabidiol (CBD). Synthetic photosensitizers include the following: RB (Rose Bengal), MB, Porphyrin derivatives, Curcumin derivatives, Methylene Blue, Indocyanine Green, Erythosine, Phenalenone derivatives, Fullerene derivatives, Xanthene derivates and combinations thereof, Indocyanine Green being particularly preferred.

In one embodiment, the mouthpiece is capable of achieving heat convection, heat radiation or both to target tissue.

In one embodiment, a part of the light sources is configured such that they emit light which achieves an antibacterial treatment of intraoral surfaces when the mouthpiece is placed in the oral cavity.

Typically, the mouthpiece is capable of producing thermal energy at 1 to 50 W, in particular at about 3 to 20 W and preferably 5 to 12 W. The total energy delivered in the mouth is, in one embodiment, between 100 J and 100 000 J, in particular between 1000 J and 30 000 J and preferably between 4000 J and 14000 J.

In one embodiment, the total radiated energy at a wavelength of between 400 nm and 1000 nm is 30 J to 30 00 0 J, in particular 300 J to 10 000 J and preferably 1000 J to 7000 J.

In one embodiment, over 50% of radiated energy is radiated at a wavelength between 400 nm and 450 nm or between 780 nm and 830 nm.

Typically, a mouthpiece as disclosed herein is capable of simultaneously stimulating dental pulp and mucous membrane with NIR light and heat generation.

The mouthpiece is capable of achieving stimulation that lasts 1 min to 60 min, preferably 2 min to 30 min and optimally 5 min to 20 min.

The kit preferably comprises a mouth rinse or mouth gel. In one embodiment, the mouth rinse or mouth gel contains a flavoring stimulating secretion of saliva, in particular the flavoring has a sour, sweet, salty or bitter taste or a taste of Umami, which stimulates secretion of saliva.

In one embodiment, the present technology provides a method of treating a patient having dry mouth syndrome. The method typically comprises the steps of subjecting the patient's salivary glands, submandibular glands or both to non-coherent light in the near-infrared range. Preferably an odontological mouthpiece is used which has one or more light sources capable for producing such light. During the treatment, the patient's salivary glands, submandibular glands or both are subjected to at least one first non-coherent light having a wavelength predominantly in the range of 350 to 450 nm, in particular 400 to 420 nm, for example at about 405 nm.

In one embodiment, the application of light will be accompanied by heat.

By the action of light and optionally heat, dilatation of blood vessels via nitric oxide release in blood vessels is achieved.

In one embodiment, by the light and optionally heat will improve microcirculation within oral tissue, in particular of the salivary and submandibular glands.

In one embodiment, the method comprises activating a hormonal or neurogenic response in the salivary glands, submandibular glands or both. comprising stimulating the salivary glands, submandibular glands or both by photobiomodulation or by heat.

In one embodiment, hyperemia will be increased.

The present technology can be used for treating a patient suffering from the Sjögren syndrome, polypharmacy patients, diabetic patients or patients having a reduced number of salivary glands in particular causing a marked decrease, temporary or permanent in saliva production.

One embodiment comprises treating a patient suffering from the Sjögren syndrome by targeting reduced production of antioxidant—i.e. by increasing the production of antioxidants in tissue—by using light at a wavelength of 350 to 450 nm, for example 400 to 420 nm, in particular about 405 nm.

The invention claimed is:

1. A kit comprising an odontological mouthpiece comprising:

one or more light sources that produce light in the near-infrared range and which, upon placement in the oral cavity of a patient, is configured to direct the light against target tissue selected from dental pulp and one or both of, salivary glands, and submandibular glands, for treatment of dry mouth syndrome in the patient, wherein at least 30% of the light, calculated from the total energy of the light, consists of light in the 780 to 830 nm range, wherein the mouthpiece is configured to direct at least 10% of the light in the 780 to 830 nm range towards dental pulp once placed in the oral cavity of the patient, and wherein the total radiated energy at wavelengths between 400 nm to 1000 nm is between 1000 J and 7000 J.

2. The kit according to claim 1, wherein the one or more light sources are configured to produce non-coherent light with photons having majority energy in the range from 1.24 eV to 2.48 eV.

3. The kit according to claim 1, wherein the one or more light sources are configured to produce light of the following energy levels: a first light with photons having a majority energy in the range from 3.5 eV to 2.8 eV, and a second light with photons having a majority energy in the range from 1.24 eV to 2.48 eV, wherein photons of the first light and the second light are simultaneously directed against the target tissue.

4. The kit according to claim 1, wherein the one or more light sources are configured to produce first light having a wavelength in the range of about 350 to 450 nm, and second light having a wavelength in the range of about 500 to 1000 nm, or a combination thereof.

5. The kit according to claim 1, wherein the one or more light sources comprise optoelectronic devices.

6. The kit according to claim 1, wherein the one or more light sources are configured to produce first light having a wavelength of 405 nm±10 nm and second light having a wavelength of 810 nm±15 nm, both the first and the second lights comprising non-coherent light.

7. The kit according to claim 1, wherein the odontological mouthpiece further comprises:

a body comprising a heat conducting material, the body comprising an upper surface and an opposite lower surface, said surfaces comprising an essentially planar portion between lingual edges and buccal or labial edges, respectively, and configured to be placed against teeth surfaces, wherein the one or more light sources are attached to the body.

8. The kit according to claim 7, wherein the lingual edges and buccal or labial edges are tilted, and wherein the one or more light sources are positioned on at least one of the lingual and buccal or labial edges.

9. The kit according to claim 1, wherein the one or more light sources subject the target tissue to light which is absorbed by erythrocytes.

10. The kit according to claim 1, wherein the one or more light sources are configured to subject the target tissue to at least light in the 350 to 450 nm range to achieve dilatation of blood vessels via nitric oxide release in the blood vessels in the patient, thus improving microcirculation.

11. The kit according to claim 1, further comprising a salivary stimulant.

12. The kit according to claim 1, further comprising at least one photosensitive substance for treating the target tissue with photodynamic therapy.

13. The kit according to claim 12, wherein the photosensitive substance is selected from the group consisting of Hypericin, curcumin, phenalenone derivatives, Cercosporin, psoralen, xanthotoxin, Angelicin, alpha-Terthienyl, Phenylthepatriyne, THC, Cannabidiol (CBD), synthetic photosensitizers, RB (Rose Bengal), MB, Porphyrin derivatives, Curcumin derivatives, Methylene Blue, Indocyanine Green, Erythosine, Phenalenone derivatives, Fullerene derivatives, Xanthene derivates and combinations thereof.

14. The kit according to claim 1, wherein the odontological mouthpiece is configured to provide heat convection, heat radiation or both to the target tissue.

15. The kit according to claim 1, wherein the mouthpiece is configured to produce thermal energy at 1 to 50 W, and wherein the total energy delivered in the mouth of the patient is between 100 J and 100,000 J.

16. The kit according to claim 15, wherein the odontological mouthpiece is configured to radiate over 50% of the total energy at a wavelength between 400 nm and 450 nm or between 780 nm and 830 nm.

17. The kit according to claim 1, wherein the odontological mouthpiece is configured to simultaneously stimulate dental pulp and mucous membrane with near infrared light and heat generation.

18. The kit according to claim 1, further comprising a mouth rinse or mouth gel that stimulates the secretion of saliva.

19. A method of treating a patient having dry mouth syndrome, the method comprising subjecting the patient's salivary glands, submandibular glands or both to non-coherent light from the odontological mouthpiece of claim 1.

20. A kit comprising an odontological mouthpiece comprising:

one or more light sources that produce light in the near-infrared range and which, upon placement in the oral cavity of a patient, is configured to direct the light against target tissue selected from the group consisting of salivary glands, submandibular glands, or both, for treatment of dry mouth syndrome in the patient, wherein the mouthpiece is configured to produce thermal energy at 1 to 50 W, wherein the total energy delivered in the mouth of the patient is between 100 J and 100,000 J, and wherein the total radiated energy at wavelengths between 400 nm to 1000 nm is between 1000 J and 7000 J.

21. A kit comprising an odontological mouthpiece comprising:

one or more light sources that produce light and which, upon placement in the oral cavity of a patient, is configured to direct the light against target tissue selected from dental pulp and one or both of salivary glands and submandibular glands, for treatment of dry mouth syndrome in the patient, wherein at least 30% of the light, calculated from the total energy of the light, comprises light in the 780 to 830 nm range, wherein the one or more light sources are configured to direct 10 to 80% of the light in the 780 to 830 nm range, calculated from the total energy of the light, towards the salivary glands, submandibular glands, or both, wherein at least 10% of the light, calculated from the total energy of the light, comprises light in the 350 to 450 nm range, and wherein the one or more light sources are configured to direct 10 to 80% of the light in the 350 to 450 nm range, calculated from the total energy of the light, towards the dental pulp.

* * * * *